| United States Patent [19] | [11] 4,315,511 |
|---|---|
| Chin | [45] Feb. 16, 1982 |

[54] ENDARTERECTOMY APPARATUS

[75] Inventor: Albert K. Chin, Stanford, Calif.

[73] Assignee: Thomas J. Fogarty, Palo Alto, Calif.

[21] Appl. No.: 73,252

[22] Filed: Sep. 7, 1979

[51] Int. Cl.³ ............................................. A61B 17/32
[52] U.S. Cl. .................................. 128/305; 15/104.16; 128/304
[58] Field of Search ............... 128/305, 754, 753, 751, 128/304; 30/316, 280, 113.1; 15/104.05, 104.16, 104.17, 104.18, 104.19, 104.02

[56] References Cited

U.S. PATENT DOCUMENTS

| 2,447,301 | 8/1948 | Wright | 30/316 X |
|---|---|---|---|
| 2,944,552 | 7/1960 | Cannon | 30/316 X |
| 3,448,741 | 6/1969 | Dennis et al. | 128/304 |
| 3,577,979 | 5/1971 | Van Der Gaast | 128/754 |
| 3,764,427 | 10/1973 | Reimels | 128/304 X |

Primary Examiner—Michael H. Thaler
Attorney, Agent, or Firm—Naylor, Neal & Uilkema

[57] ABSTRACT

A cutting annulus which is radially expansible is employed to achieve complete removal of arteriosclerotic material from occluded arteries.

2 Claims, 9 Drawing Figures

ENDARTERECTOMY APPARATUS

BACKGROUND OF THE INVENTION

The invention relates to an improved means comprising a radially resilient cutting loop for excising an extended length of arteriosclerotic material from the lumen of an occluded artery.

The present invention constitutes an improvement upon the basic endarterectomy apparatus shown and described in commonly owned co-pending application, Ser. No. 060,000, filed July 23, 1979, now abandoned.

Other than said co-pending application and the two U.S. Patents identified therein as prior art, I know of no art, prior or otherwise, which is material as to the subject invention.

SUMMARY OF THE INVENTION

With the fixed cutting loop of the apparatus of the aforementioned application, it is possible for the cutting edge of the loop to deviate from the desired cutting line between the layers of atheroma and artery. Such a deviation could cause the loop to pierce through the atheroma into the lumen of the artery, thereby detaching only part of the atheroma. This is prevented by the improved cutting loop of the invention, the loop being an expansible one which exerts a constant outwardly directed pressure to cause it to naturally seek out the largest diameter possible as it travels over the length of the atheroma, thereby minimizing the possibility of a partial removal of the atheroma.

The principal object of the invention is to provide an improved endarterectomy cutting loop which is adapted to be passed through a diseased artery while it tends to radially expand against the lumen of the artery.

A further object of the invention is to provide an improved process for effecting full removal of an atheroma from an artery.

DESCRIPTION OF THE PREFERRED EMBODIMENT

Figure 1:
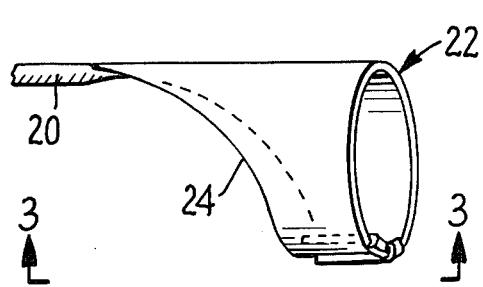
FIG. 1 is a view in perspective of one embodiment of the improved cutting loop of the invention.

In the drawing, the artery 10 contains a section of arteriosclerotic material 12 and is provided with a proximal incision 14 adjacent one end of the material 12 and a distal incision 16 adjacent the other end of this material. Preparatory to the application of the apparatus to the artery 10, an annular plane 17 is cut around the proximal end of the atheroma 12.

The apparatus comprises a catheter 18, a wire 20, and an annular cutting loop 22. The manner of emplacement of the cathether 18 and wire 20 between the atheroma 12 and the lumen of artery 10 is described in detail in the previously mentioned patent application. Also described therein are the specifications as to materials which may be suitably used for the catheter 18, wire 20 and loop 22. Wire 20 is preferably made of stainless spring steel. The cutting knife for loop 22 is preferably made from a section of resilient spring material, such as plastic or stainless steel, suitably connected to the wire 20. The differences between the subject apparatus and process inventions and those of said previously mentioned patent application reside in the differences between the respective cutting loops employed and the consequent new and improved function and manner of operation of the loop.

Figure 2:
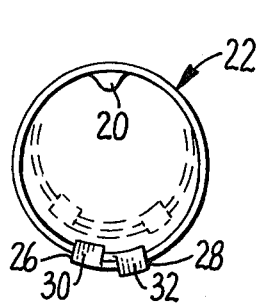
FIG. 2 is a view in right elevation of the loop of FIG. 1.
Figure 3:
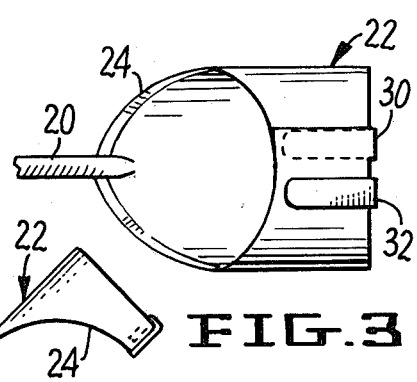
FIG. 3 is a view taken along lines 3—3 of FIG. 1.

The annular loop 22 is provided with cutting edge 24. The loop is longitudinally split along its short side. The resulting edges 26 and 28 are then made to extend past each other, i.e., overlapped, as shown in FIG. 2. The loop is provided with integral tabs 30 and 32, the former being located at the outer edge 26 of the loop and the latter being located at the inner edge 28 of the loop. These tabs are bent back over the adjacent end portions of the loop to insure that the overlapped ends of the loop are constrained to remain in the overlapped condition. FIG. 2 illustrates in solid outline the normal position of the restraining tabs 30, 32 and shows in dotted outline a positional condition of the two tabs when the loop is under substantial radial compression.

Figure 4:
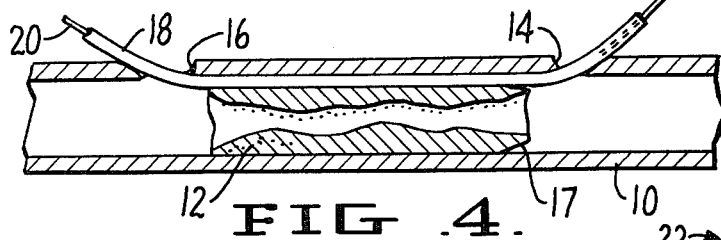
FIG. 4 is a view in diametral section through an occluded artery illustrating preliminary emplacement of the apparatus with reference to the artery.
Figure 5:
FIG. 5 is a similar view showing the loop in compressed condition by forceps just before insertion of the loop into the artery.
Figure 6:
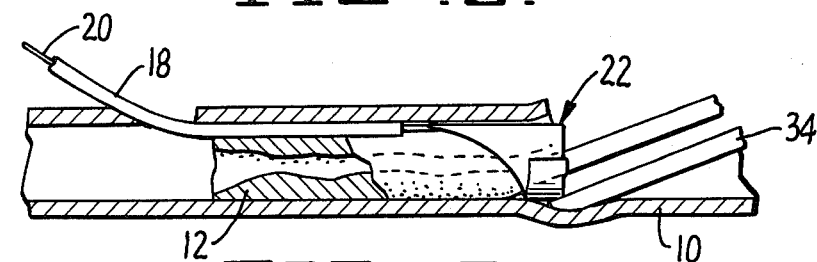
FIG. 6 is a view similar to that of FIG. 5, but showing the compressed loop emplaced in the artery.
Figure 7:
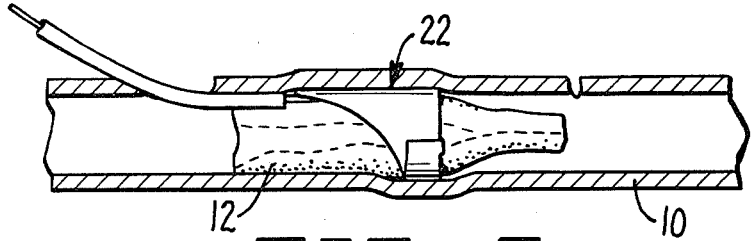
FIG. 7 is a similar view showing the atheroma as being partially excised.
Figure 8:
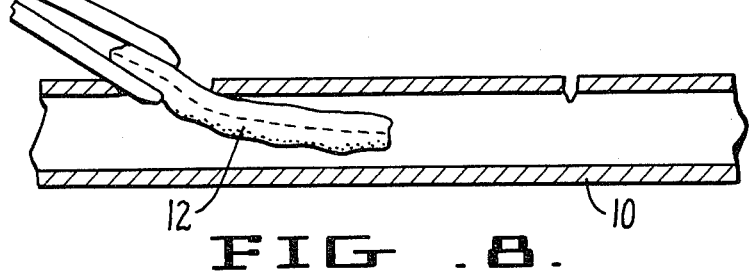
FIG. 8 is a similar view illustrating removal of the detached atheroma from the artery.

With the apparatus in the condition shown in FIG. 4, the cutting loop 22 is manually compressed radially, e.g., to the dotted line position shown in FIG. 2, and forceps 34 are then employed to maintain the loop under compression until after it has been inserted through the incision 14 and into the position shown in FIG. 6. The forceps are then removed and the loop partially expands to fit into the cutting plane 17. The loop remains under compression, however, and tends to expand radially against the lumen of the artery, as shown in FIG. 7, during the entire course of it being drawn along the length of the atheroma 12. This spring action of the loop ensures that the loop exerts a constant outward pressure, naturally seeking as large a diameter as possible as it proceeds along the length of the atheroma. A complete removal of the atheroma is thereby ensured.

Figure 9:
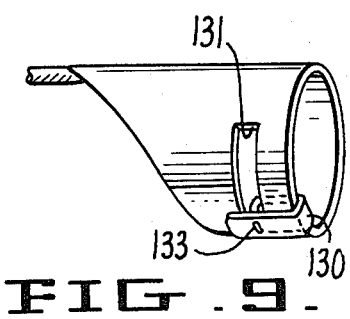
FIG. 9 is a view in perspective of another embodiment of the cutting loop of the invention.

A further embodiment of the cutting loop is shown in FIG. 9. Only one tab 130 is provided. It is shown as being integral with the outside of the two overlapped portions of the loop. The inside of the two overlapped portions is provided with a slot 131 which is closed at both ends. The end of the tab 130 is bent outwardly through the slot 131 and is attached, as by soldering 133 to the outer end portion of the loop. The loop is thereby rendered radially compressible while its ends are secured together to prevent them from getting out of their overlapped condition.

It is to be pointed out that the loop could be installed in the artery without using forceps to hold it in compressed condition. Means could be provided to initially clamp or latch the loop in compressed condition and the clamping or latching means could then be released after the loop has been inserted into the artery.

CONCLUSION

Although preferred and alternative embodiments of the invention have been illustrated and described, it is to be understood that the invention is not to be limited to the specifics of any of such embodiments, but rather is to be defined only by the appended claims.

What is claimed is:

1. An endarterectomy instrument comprising: an annular knife having a cutting edge at one end thereof directed longitudinally of the knife and through a full 360° of its periphery; a wire carrier attached tangentially to said knife and extending away from said one end in the direction of said cutting edge whereby said knife may be pulled along an occluded artery to excise an arteriosclerotic occlusion therefrom, said knife being split longitudinally and having overlapped end portions to thereby enable said knife to be yieldingly compressible radially for insertion within an artery and to thereafter enable said knife to apply a substantially constant outwardly directed pressure against and through a full 360° of the interior circumference of said artery as said occlusion is being excised to thereby maintain the knife against deviation from axial alignment with the artery; and, means carried by said knife to prevent said end portions from separating while permitting sliding movement of said end portions relative to each other during compression and expansion of said knife.

2. The instrument of claim 1, said means comprising a tab member carried by one of said overlapped end portions extending into overlying relation with a portion of the other of said overlapped portions.

* * * * *